United States Patent [19]

Sneider

[11] 4,351,336
[45] Sep. 28, 1982

[54] TWIST BOTTLE DISPENSER

[76] Inventor: Vincent R. Sneider, 3422 Hallcrest Dr., NE., Atlanta, Ga. 30319

[21] Appl. No.: 174,806

[22] Filed: Aug. 4, 1980

[51] Int. Cl.³ .............................................. A61M 1/00
[52] U.S. Cl. .................................... 128/232; 128/274
[58] Field of Search ................ 128/232, 274, 251, 224

[56] References Cited

U.S. PATENT DOCUMENTS

| | | | |
|---|---|---|---|
| 3,993,070 | 11/1976 | Sneider | 128/251 |
| 4,168,032 | 9/1979 | Sneider | 128/232 X |
| 4,200,097 | 4/1980 | Hobbs, Jr. et al. | 128/251 |
| 4,230,111 | 10/1980 | Plazza et al. | 128/251 X |

*Primary Examiner*—John D. Yasko
*Attorney, Agent, or Firm*—Ralph R. Roberts

[57] ABSTRACT

A dispenser, such as a syringe or the like, is disclosed for dispensing liquids or other fluid material. A generally tubular side wall has closed lower and upper ends with discharge means in the upper end. The tubular side wall is formed by a plurality of spiral ribs for twisting and collapsing the dispenser about its longitudinal axis to dispense the fluid material therefrom through the discharge means. The spiral ribs extend into and through the closed ends of the dispenser to facilitate dispensing substantially the entire material therefrom by twisting action of the dispenser. The ribs have generally flat outer surfaces separated by V-shaped grooves whereby when collapsed the dispenser forms a substantially stable handle with the flat outer surfaces disposed in substantially side-by-side abutment. The dispenser is formed as an integral molded and prefilled construction, including a frangible cap on a threaded neck which forms the discharge means. A valve construction also is disclosed for use with a syringe nozzle.

10 Claims, 9 Drawing Figures

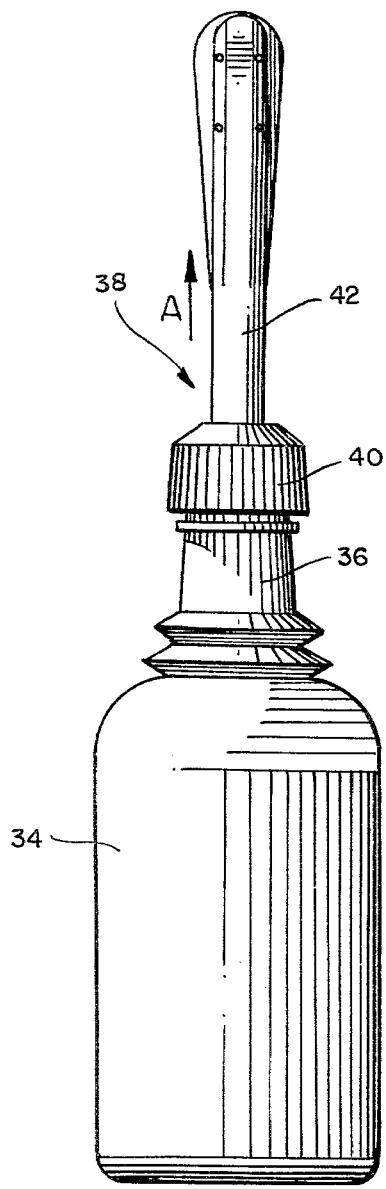
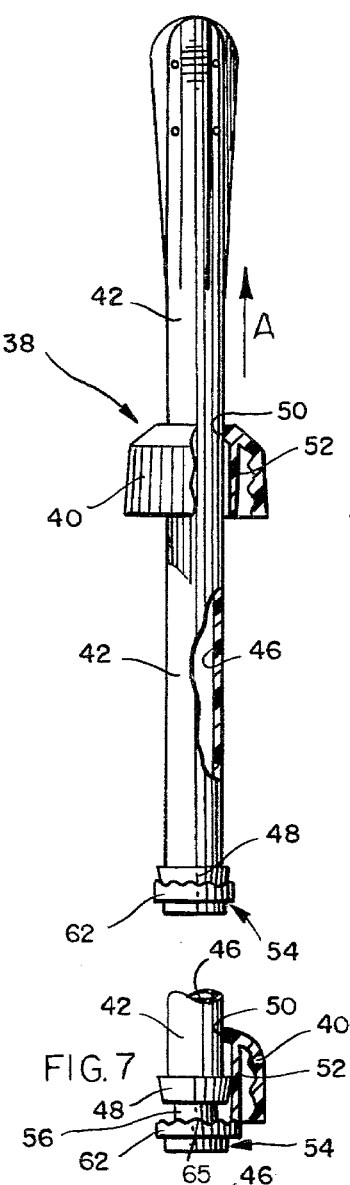
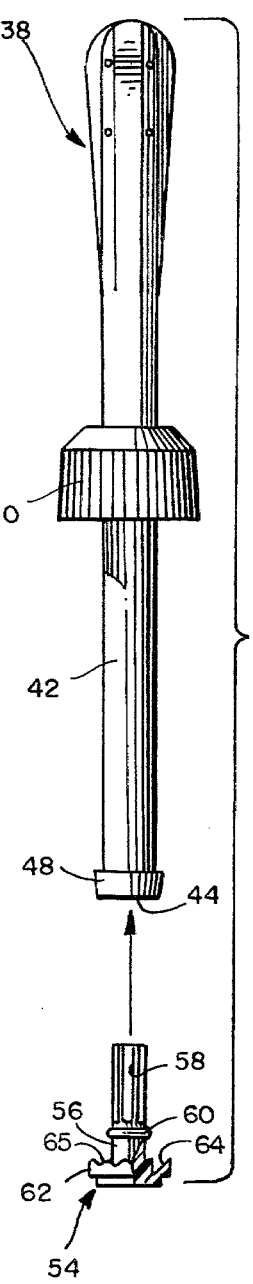

TWIST BOTTLE DISPENSER

BACKGROUND OF THE INVENTION

This invention relates to dispensers for liquids or other fluid material and, particularly, to a dispenser which is readily adaptable for use as a syringe for vaginal douche, swab, or like applications.

It has become increasingly important to provide vaginal applicators which are economical to manufacture and which utilize inexpensive materials so that the applicators may be disposable, that is employed for a single use and then discarded. It also is important to provide a vaginal applicator which is inherently hygienic. To this end, such applicators have become increasingly popular which are manufactured and prefilled at a manufacturing plant under sanitary conditions, then sealed by integral molding until ready for use. The containers of such applicators can be prefilled with medicaments or simply with cleansing and rinsing solutions.

Some examples of such integrally molded and prefilled vaginal applicators presently on the market are those under the names of "Feminique" TM of Ennis Laboratories, Edison, N.J. and "Massengill" TM of Beecham Products, Pittsburgh, Pa. With these and other similar products presently on the market, a premeasured volume of liquid is emphasized. However, it is practically impossible to dispense the entire volume of liquid from the dispenser during normal use. Most such dispensers are collapsible, but the dispensers cannot be completely collapsed so as to dispense substantially the entire premeasured volume of liquid from the dispenser.

Attempts have been made in the dispenser art to provide a sort of twisting action to dispensers in order to discharge fluid material therefrom. For instance, U.S. Pat. No. 2,723,779 to C. Parker et al., dated Nov. 15, 1955, shows a flexible container and dispenser in which a so called "twist" will be produced in the container to reduce the volume thereof. However, the container specifically is provided with a relatively rigid base portion on which the container may rest and upon which it will stand erect. Again, as with commercially available vaginal applications, it is practically impossible to dispense substantially the entire volume of material from the dispenser. This is particularly problematic when a premeasured volume of liquid is desirable. U.S. Pat. No. 2,661,422 to J. L. Jones, dated Nov. 4, 1952, shows vaginal applicators which have various constructions, including accordion or twisting liners within rigid outer tubes. Such applicators are too complicated, involve multiple components, and are not readily applicable for prefilled, disposable dispensers.

The present invention is designed to provide a new and improved dispenser for liquid or other fluid materials, which is readily applicable for use as a syringe for vaginal douche, swab, or like applications, and which solves the problems outlined above.

SUMMARY OF THE INVENTION

An object, therefore, of the present invention is to provide a new and improved dispenser for liquids or other fluid material.

Another object of the present invention is to provide a dispenser of the character described which is readily applicable for use as a syringe for vaginal douche, swab, or like applications.

A further object of the invention is to provide a dispenser of the character described and which employs a twisting action for dispensing substantially the entire volume of material from the dispenser.

In the exemplary embodiment of the invention, the dispenser includes a generally tubular side wall having a closed lower end and a closed upper end with discharge means in the upper end. The side wall is formed by a plurality of spiral ribs for twisting and collapsing the dispenser about its longitudinal axis to dispense the material therefrom through the discharge means. The spiral ribs extend into and through the closed lower end of the dispenser to facilitate dispensing substantially the entire volume of material from the dispenser by a twisting action. Preferably the spiral ribs also extend into and through the closed upper end of the dispenser.

As shown herein, the spiral ribs have generally flat outer surfaces which are separated by V-shaped grooves formed between the flat outer surfaces. With this construction, when collapsed the dispenser forms a substantially stable handle for easy grasping by a user, with the flat outer surfaces disposed in substantial side-by-side abutment. This is important when the dispenser is used as a vaginal douche, swab, or the like.

The dispenser is shown formed as an integral molded and prefilled construction, with the discharge means comprising a threaded neck for receiving a complementarily threaded nozzle, swab, or the like. A frangible cap is molded integrally with the end of the threaded neck for opening the dispenser to discharge fluid therefrom through the threaded neck and associated attachment.

A valve construction also is disclosed for use with a syringe or like dispensing means which includes an axially movable nozzle. The nozzle has a tubular portion with an inner open end communicating with an interior axial bore through the tubular portion. The valve construction includes a valve plug reciprocally mounted within the axial bore of the nozzle at its open end and has fluid passage means formed along the exterior of the plug for flow of fluid therethrough along the interior walls of the axial bore. First seal means, in the form of an integral annular ring, surrounds the valve plug axially outwardly of the fluid passage means, for sealing engagement with the interior walls of the axial bore. Second seal means, in the form of an integral annular flange, protrudes radially outwardly of the valve plug, axially outwardly of the first seal means, for sealing engagement with the open end of the tubular portion of the nozzle.

Other objects, features and advantages of the invention will be apparent from the following detailed description taken in connection with the accompanying drawings.

DESCRIPTION OF THE DRAWINGS

FIG. 5 is an elevational view of another form of dispenser, incorporating an axially movable nozzle for the valve construction of the present invention;

FIG. 6 is an elevational view of the nozzle shown in FIG. 5, with the valve construction of the present invention in sealing engagement with the inner open end thereof;

FIG. 7 is a fragmented elevational view of the inner end of the nozzle of FIG. 6, with the valve construction in a first stage of opening;

FIG. 8 is a view similar to that of FIG. 7, with the valve construction in its completely open position; and FIG. 9 is an exploded elevational view of FIG. 6, with the valve plug removed to facilitate the illustration.

DETAILED DESCRIPTION OF THE INVENTION

Figure 1:
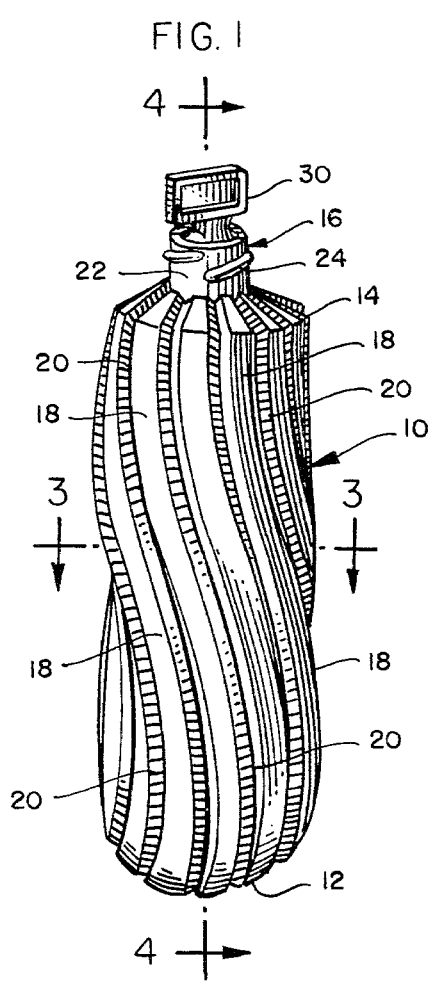
FIG. 1 is a perspective view of the twist dispenser of the present invention, in a prefilled unopened condition.

Referring to the drawings in greater detail, and first to FIG. 1, a dispenser for liquids or other fluid material is shown and includes a generally tubular side wall, generally designated 10. The tubular side wall has a closed lower end 12 and a closed upper end 14, the latter being provided with discharge means, generally designated 16.

Side wall 10 is formed by a plurality of spiral ribs which have generally flat outer surfaces 18. The ribs are separated by generally V-shape grooves 20. As seen in FIG. 1, the ribs and grooves extend into and through the closed lower and upper ends 12 and 14, respectively, to facilitate dispensing substantially the entire volume of material from the dispenser by a twisting action thereof. That is, the ribs and grooves are formed through the junctures between the tubular side wall and the upper and lower ends of the dispenser. At the upper end 14, the ribs and grooves extend completely across the upper end toward the discharge means 16.

Figure 2:
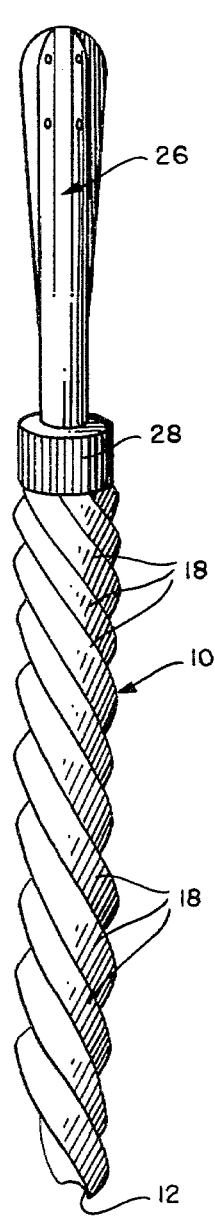
FIG. 2 is a perspective view of the dispenser in a twisted, collapsed condition and with a douche nozzle threaded onto the end thereof.
Figure 3:
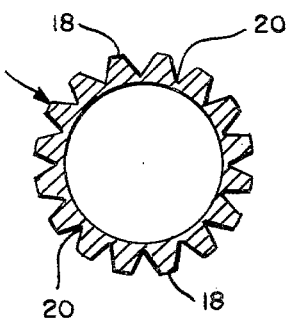
FIG. 3 is a horizontal sectional view taken generally along the line 3—3 of FIG. 1.
Figure 4:
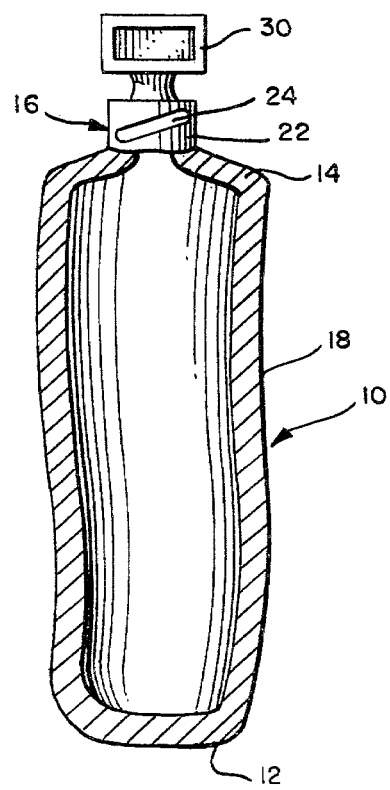
FIG. 4 is a vertical sectional view taken generally along the line 4—4 of FIG. 1, but through a single spiral rib.

With the ribbed construction of side wall 10 as described above, and referring to FIG. 2, when the dispenser is collapsed by a twisting action, it forms a substantially stable handle with the flat outer surfaces 18 of the ribs disposed in substantial side-by-side abutment. This is particularly important when the dispenser is used as a syringe or vaginal applicator, such as a douche, swab, or the like.

For such uses, discharge means 16 (FIG. 1) comprises a neck 22 having external thread means 24. A douche nozzle, generally designated 26 (FIG. 2), of known construction, can be threaded onto neck 22 by means of an appropriate internally threaded cap portion 28.

In the preferred embodiment of the invention, the dispenser is fabricated of an appropriate plastic material, as an integral molded and prefilled construction. To this end, a frangible cap 30 is molded integrally with the top of neck 22 and can be removed by holding the neck and breaking the cap therefrom by a twisting motion. After the cap is frangibly removed, douche nozzle 26 can be threaded onto the neck and the dispenser can be twisted, by means of its spiral construction, to dispense substantially the entire volume of material therefrom through the douche nozzle. Of course, other attachments, such as swab attachments or the like, can be threaded onto the dispenser as described above for appropriate applications.

Referring to FIGS. 5-9, a valve construction is shown for use with a syringe or like dispensing means. The syringe includes a flexible, collapsible container 34 having a neck portion 36 onto which is threaded a nozzle assembly, generally designated 38. The nozzle includes an internally threaded cap member 40 of known construction and which is threaded onto neck 36 of container 34. The nozzle assembly further includes a nozzle member having a tubular portion 42 which is provided with an inner open end 44 (FIG. 9). The inner open end is in fluid communication with an interior axial bore 46 (FIG. 6) of tubular portion 42. The tubular portion is slidably movable within cap member 40 whereby the inner open end 44 of the nozzle assembly is disposed within container 34. An annular flange 48 extends about tubular portion 42 at the open end 44 thereof.

Referring to FIG. 6, cap member 40 has a central aperture 50 within which tubular portion 42 is slidably received in sealing engagement therewith. The cap member also has an interior cylindrical portion 52 which depends from the underside of the cap spaced inwardly from the outer wall of the cap. This annular flange 48 may be integrally formed on the end 44 of the tubular portion of the nozzle after the cap member 40 is mounted on this tubular portion. This annular flange alternately may be made as a separately formed member and secured at the end of the tubular portion of the nozzle. Alternately, the nozzle 26 may also be sufficiently resilient so that the nozzle 40 may be manipulated through the aperture 50. It is also contemplated that the flange portion 48 be made with the end seatable in the groove 64 but having no protrusion adapted to engage the aperture 50 and inhibit or limit the outer movement of the tubular portion 42.

The valve construction, generally designated 54, of the present invention is shown with particularity in FIGS. 6-9. More particularly, the valve construction includes a valve plug 56 which is slidably mounted within axial bore 46 at the open end 44 of tubular portion 42 of the nozzle assembly. The valve plug has a plurality of axial passages 58 (FIGS. 8 and 9) formed in and along the exterior surface of the plug for the flow of fluid from container 34 therethrough and into tubular portion 42 of nozzle assembly 38 for dispensing therefrom.

First seal means in the form of an annular ring 60 (FIGS. 8 and 9) surrounds valve plug 56 axially outwardly of and below fluid passages 58 for sealing engagement with the interior walls of axial bore 46.

Second seal means which includes an annular flange 62 is formed integrally with the valve plug 56 at the outer end thereof. Flange 62 has an annular groove 64 (FIG. 9) facing the open end 44 of the tubular portion 42 of nozzle assembly 38. This groove is tapered for receiving the open end of tubular portion 42, and, to this end, flange 48 at the open end of the tubular portion is wedge shaped complementarily with the tapered configuration of groove 64 for tight sealing engagement therewith.

It is to be noted in FIGS. 6, 7, 8 and 9 that the annular flange 62 at its upward and outer edges exterior of the tapered groove 64 is formed with a plurality of scallops 65. These scallops provide fluid pathways between plug 54 and the lower end 44 of the annular flange 48. The scallops are shown on the plug 54 with collar 52 having a surface in a common plane but this does not preclude the scallops being formed on the collar 52 and flange 62 made with a smooth surface. As seen in FIG. 9, plug 54 is made as a solid member with no interior passageways. Fluid is moved exteriorally past the plug 54 and through grooved passageways 58 in the stem portion and into the nozzle 26. As depicted, there is no provision or contemplation for reestablishing the valve to a closed condition in which the annular flanged end portion is seated in the groove 64.

The operation of valve construction 54 in relation to the syringe and nozzle assembly 38 shown in FIGS. 5-9 will now be described. In a stored or inoperative, nondispensing condition, nozzle assembly 38 is threaded onto container 34 as shown in FIG. 5, with the nozzle assembly and valve construction 54 in the condition shown in FIG. 6. In order to condition the nozzle assembly and valve construction for use to dispense liquid from the container, tubular portion 42 is pulled outwardly in the direction of arrow A (FIGS. 5 and 6) axially in relation to cap member 40 and container 34. During this movement, tubular portion 42 retains its seal with the central bore 50 of cap member 40. The tubular portion is moved outwardly in the direction of arrow A until the annular flange 62 of valve plug 56 abuts against the edge of the interior cylindrical portion 52 of cap member 40. With the valve plug thus stopped by the cap member, further movement of the tubular portion 42 axially outwardly of the cap member causes the valve plug to move sequentially from its fully closed position to the positions shown in FIGS. 7 and 8. In the intermediate position shown in FIG. 7, the second seal means provided by annular flange 62 and groove 64 is released from sealing engagement with the wedge shaped flange 48 at the inner end of tubular member 42. However, the first seal means provided by annular ring 60 still remains sealed with the interior walls of axial bore 46. Further outward axial movement of tubular member 42 causes valve plug 56 to move to its fully opened position shown in FIG. 8, wherein fluid passages 58 are exposed exteriorly of but still in fluid communication with the open end 44 of the tubular nozzle member. The tubular nozzle member cannot not be completely withdrawn from cap member 40 and container 34 because flange 48 abuts against the interior of cap member 40 about the central bore 50 therethrough, as see in FIG. 8.

With the valve construction 54 of the present invention, primary and secondary seal means is provided. The primary seal means is provided by the tight wedging engagement between flange 48 of tubular nozzle member 42 within the tapered groove 64 of the valve plug. However, during manufacture or assembly of the nozzle onto the container, the valve plug may be accidentally moved slightly outwardly of the nozzle assembly in an axial direction. Should this occur, the secondary seal means provided by annular ring 60 still affords protection from leakage by engagement of the annular ring with the interior walls of axial bore 46 of the tubular nozzle member 42.

If desired, the container may be refilled after use by effecting disassembly whereat plug 54 is again pushed into the sealed condition of FIG. 7. After reassembling with the desired quantity of fluid therein the use operation proceeds as above described.

It will be understood that the invention may be embodied in other specific forms without departing from the spirit or central characteristics thereof. The present examples and embodiments, therefor, are to be considered in all respects as illustrative and not restrictive, and the invention is not to be limited to the details given herein.

I claim:

1. A syringe or like dispensing apparatus characterized as having an axially movable nozzle with a contoured exterior end with discharge means, this nozzle having a tubular stem portion with an interior axial bore, this tubular portion having a finished inner end and providing therewith a sealing end portion, and a cap member associated with said nozzle and having a retaining aperture sized to be slidable along the tubular stem portion of the nozzle, said cap member having a tubular collar member portion extending from the retaining aperture and for a determined distance and on the end of this tubular collar portion finished so as to provide a stop end substantially normal to the axis of the collar member, and with said cap member having means for securing the cap member and nozzle to a fluid container for the discharge of a fluid in said container, the syringe having a valve construction selectively actuatable for the discharge of the fluid contents of the container, the valve construction including:

(a) a valve plug having a stem portion slidable within said axial bore of the tubular stem portion of the nozzle, the stem portion of the valve plug having longitudinal fluid passageways formed along and in the exterior surface of said stem portion, these passageways providing means for conducting fluid from the container to the interior of the nozzle when these passageways are exposed to the fluid within the container;

(b) a first seal means on said valve plug and disposed circumferentially around said valve plug and below said longitudinal passageways, this seal means adapted to engage the interior bore of the tubular portion of the nozzle and slide therealong and therein;

(c) a second seal means formed on said valve plug and at a determined distance from said first seal means and substantially at the end opposite the stem portion, this seal means extending outwardly and having surface means disposed to engage the finished stop end on the nozzle to effect a fluid seal;

(d) an annular flange portion formed on said valve plug and outwardly of said second seal means and sized and disposed to engage the stop end of the collar member of the cap, and (e) cooperating means formed on the stop end of the collar and the annular flange of the valve plug, said cooperating means providing a fluid pathway from the container to the exterior of the valve plug, and the first and second seal means is effective when the valve plug is fully inserted and there is no fluid flow through the cooperative means to the interior of the nozzle, outward partial movement of the nozzle makes the second seal means ineffective while the first seal prevents fluid flow into the fluid passageways and further outward movement of the nozzle renders the first seal means ineffective and no longer inhibits fluid flow as and when the first seal means is moved from in way of the interior bore of the tubular portion of the nozzle and fluid flows into the longitudinal fluid passageways formed in the stem of the valve plug and into the interior of the nozzle for discharge therefrom.

2. The valve construction of claim 1 in which the stop end of the nozzle is formed with a projecting annular flange providing therewith a shoulder disposed toward the retaining aperture in the cap member, this shoulder adapted and sized to engage the retaining aperture in the cap member and thereby to inhibit further outward movement of the nozzle.

3. The valve construction of claim 1 in which the cooperative means formed in the stop end of the collar of the cap member and the annular flange of the plug are scallops.

4. The valve construction of claim 3 in which the scallops are formed in the annular flange of the valve plug.

5. The valve construction of claim 1 wherein said first seal means comprises an annular ring formed integral with said valve plug.

6. The valve construction of claim 1 wherein said second seal means comprises an annular flange formed integral with said valve plug.

7. The valve construction of claim 6 wherein said annular flange has an annular groove facing said open end of said nozzle, this annular groove in said valve plug disposed to enter and engage said groove to provide a sealing engagement within said groove.

8. The valve construction of claim 7 wherein said annular groove in said valve plug is tapered for receiving said open end in a wedge engagement.

9. In combination with the valve construction of claim 8, a nozzle wherein said open end thereof is wedge shaped complementarily with said tapered groove.

10. The valve construction of claim 8 wherein said first seal means comprises an annular ring formed integral with said valve plug.

* * * * *